United States Patent

Clark et al.

[11] Patent Number: 6,010,837
[45] Date of Patent: Jan. 4, 2000

[54] SILVER HALIDE PHOTOGRAPHIC ELEMENT COMPRISING IMAGE DYE-FORMING COUPLERS

[75] Inventors: Bernard A. Clark, Maidenhead; Michael W. Crawley, Kingswood; Jane S. Boff, St. Albans; Christina M. Watts, Harrow Weald, all of United Kingdom; Stephen P. Singer, Spencerport, N.Y.; Paul L. Stanley, Harrow, United Kingdom

[73] Assignee: Eastman Kodak Company, Rochester, N.Y.

[21] Appl. No.: 08/842,281

[22] Filed: Apr. 23, 1997

[30] Foreign Application Priority Data

Apr. 30, 1996 [GB] United Kingdom .................. 9608886

[51] Int. Cl.[7] .............................. G03C 1/08; G03C 7/26; G03C 7/32
[52] U.S. Cl. ..................... 430/555; 430/554; 430/502; 430/503
[58] Field of Search ..................... 430/554, 535, 430/502, 503

[56] References Cited

U.S. PATENT DOCUMENTS

| | | | |
|---|---|---|---|
| 3,738,840 | 6/1973 | Anderson | 430/502 |
| 4,021,238 | 5/1977 | Hayashi et al. | 430/543 |
| 5,447,831 | 9/1995 | Singer et al. | 430/504 |
| 5,563,026 | 10/1996 | Singer | 430/555 |
| 5,601,968 | 2/1997 | Weber et al. | 430/555 |
| 5,610,003 | 3/1997 | Lussier | 430/555 |
| 5,667,946 | 9/1997 | Boff et al. | 430/555 |

FOREIGN PATENT DOCUMENTS

| | | |
|---|---|---|
| 58/117542 | 3/1991 | Japan . |
| 5/100388 | 11/1992 | Japan . |
| 2125570 | 10/1986 | United Kingdom . |
| 1501604 | 4/1993 | United Kingdom . |
| 2081464 | 2/1995 | United Kingdom . |

*Primary Examiner*—Geraldine Letscher
*Attorney, Agent, or Firm*—Arthur E. Kluegel

[57] ABSTRACT

The invention provides a photographic element comprising a silver halide emulsion layer having associated therewith an image dye-forming coupler of formula (I):

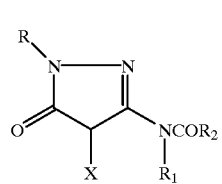

wherein X is H or a coupling-off group, R is H; or R, $R_1$ and $R_2$ are the same or different and are coupler-modifying functional groups (with the provisos that (a) the moiety $N(R_1)COR_2$ may not be a carbamate, ureido or imido and (b) $R_1$ and $R_2$ may not both be phenyl or substituted phenyl); or $R_1$ and $R_2$ taken together with the nitrogen atom and the carbonyl group form a 5–10 membered heterocyclic ring which may contain one or more further heteroatoms selected from N, O and S, said heterocyclic ring being unsubstituted or substituted with one or more coupler-modifying functional groups, with the proviso that the ring is not a cyclic carbamate, ureido or imido; and wherein the coupler forms a dye with a peak absorption less than 565 nm.

17 Claims, 1 Drawing Sheet

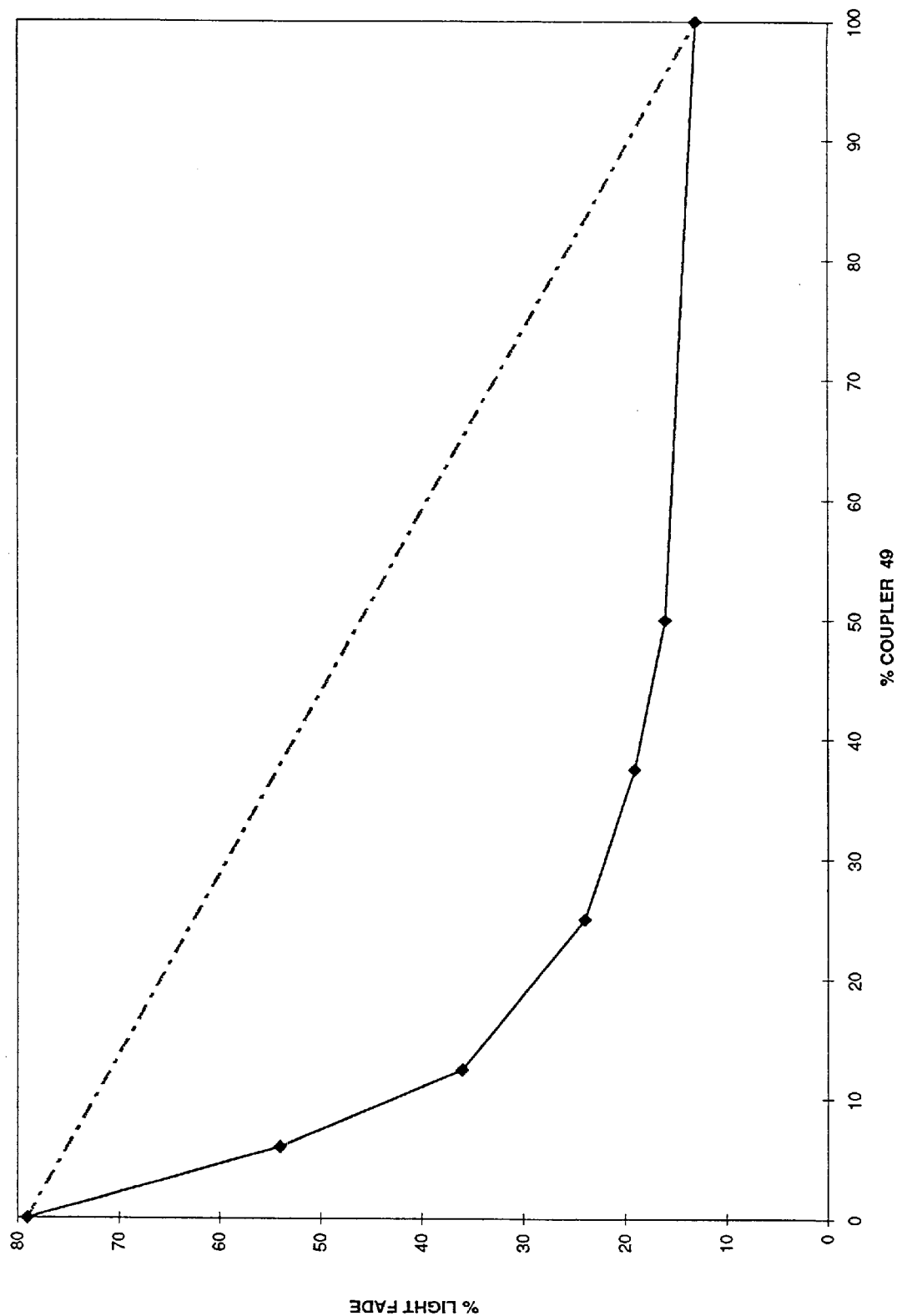

SILVER HALIDE PHOTOGRAPHIC ELEMENT COMPRISING IMAGE DYE-FORMING COUPLERS

FIELD OF THE INVENTION

The present invention relates to silver halide photographic elements comprising image dye-forming couplers, hereinafter called "couplers", for use in chromogenic development processes. In particular the present invention relates to elements containing such image dye-forming couplers of the pyrazolone type which form azamethine dyes on reaction with oxidized color developers. The present invention also embraces couplers in accordance with the present invention.

BACKGROUND OF THE INVENTION

Magenta couplers for use in commercial photographic materials, including films and papers, are usually drawn from the pyrazolone and pyrazolotriazole classes, in view of the stability of these compounds in raw-stock and their rapid and efficient reaction with oxidized color developers. Dyes derived from commercial pyrazolone and pyrazolotriazole magenta couplers also have acceptable spectrophotometric curve shapes.

Pyrazolone magenta couplers having secondary amino substituents in the 3-position have been used commercially. These couplers have been prepared via synthetic routes which involve acylation of the secondary amino group in the 3-position to form an amido protecting group, followed by removal of the N-acyl group to form the coupler materials; see e.g. JP-A-52/091862 which discloses the conversion of a nitro substituent of a phenyl ring on the 3-nitrogen atom to a tetradecanamide moiety, while the 3-secondary amino is protected by acylation (also see DE 2703589, DE 2651363).

U.S. Pat. No. 5,447,831 discloses the use of certain acyl compounds as ancillary couplers to the main image-dye forming couplers to improve printer compatibility, the couplers forming dyes having a peak absorption between 565–600 nm.

JP-A-58/117542 disloses N-acyl pyrazolones having a pentachlorophenyl substituent, which generate a dye having a peak absorption of 610 nm, giving improved color reproducibility.

U.S. Pat. No. 4,021,238 discloses fogged emulsion layers containing an N-phenyl-N-benzoyl pyrazolone that forms a nondiffusible colored dye with oxidized color developer, giving improved color reproduction and high sharpness.

JP-A-05/100388 discloses N-acyl pyrazolones which provide formaldehyde image stability, the compounds having a carbamate or ureide moiety attached to the pyrazolone ring.

DE Offenlegungschrift No 2018562 discloses pyrazolones substituted with an imide moiety, which provide improved viscosities of silver halide emulsions as compared with those containing commercial couplers.

A disadvantage which is associated with magenta couplers of the pyrazolone and pyrazolotriazole types which have hitherto been used commercially in the art, is that the azamethine dyes formed by the condensation of these couplers with oxidized arylamine developers are generally less stable to actinic light as compared with the dyes derived from commercial yellow and cyan couplers.

It is an object of the present invention therefore to provide elements containing image dye-forming couplers which form azamethine dyes that are more stable to exposure to actinic radiation as compared with known pyrazolone and pyrazolotriazole couplers, and which at the same time retain the advantageous properties of these classes of couplers.

SUMMARY OF THE INVENTION

The invention provides a photographic element comprising a silver halide emulsion layer having associated therewith an image dye-forming coupler of formula (I):

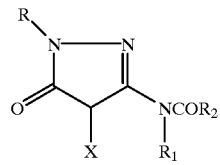

wherein X is H or a coupling-off group, R is H; or R, $R_1$ and $R_2$ are the same or different and are coupler-modifying functional groups (with the provisos that (a) the moiety $N(R_1)COR_2$ may not be a carbamate, ureido or imido and (b) $R_1$ and $R_2$ may not both be phenyl or substituted phenyl); or $R_1$ and $R_2$ taken together with the nitrogen atom and the carbonyl group form a 5–10 membered heterocyclic ring which may contain one or more further heteroatoms selected from N, O and S, said heterocyclic ring being unsubstituted or substituted with one or more coupler-modifying functional groups, with the proviso that the ring is not a cyclic carbamate, ureido or imido; and wherein the coupler forms a dye with a peak absorption less than 565 nm.

Dyes formed by elements of the present invention using couplers of formulae (I) and (I)' have been found to exhibit substantially improved stability to exposure to actinic light as compared with known pyrazolone and pyrazolotriazole type magenta couplers. In some instances, dyes derived from the couplers in accordance with the present invention may exhibit an improved stability to actinic light up to 30 times better as compared with known pyrazolone and pyrazolotriazole couplers as measured by a % dye light fade test as described hereinafter; a typical improvement will be about 7–10 times more stable.

When couplers of the present invention are combined with other main image dye-forming couplers, mole ratios of coupler of the invention of less than 30% can give significant reductions in light fade.

BRIEF DESCRIPTION OF THE DRAWINGS

The FIGURE shows % dye light fade of various mole ratios of a coupler of the invention with another (control) main image-dye-forming coupler.

DETAILED DESCRIPTION OF THE INVENTION

Generally the peak absorption will be in the range 530 to 565 nm, more specifically 540 to 565 nm.

Said coupling-off group is a group adapted to split off from the coupler as a result of the reaction between the coupler and the oxidation product of an arylamine color developer. A coupler-modifying functional group is any substituent which by its presence in the coupler structure influences the photographic or physical properties of the coupler or a dye derived from the coupler.

According to an aspect of the present invention there is provided a multi-color photographic material comprising a support bearing yellow, magenta and cyan image dye-forming units comprising at least one blue, green or red sensitive silver halide emulsion layer having associated therewith at least one yellow, magenta or cyan image dye-forming coupler respectively, wherein at least one image dye-forming coupler is a coupler of formula (I) in accordance with the present invention.

The present invention thus comprehends an image dye-forming coupler of the pyrazolone type which comprises a tertiary N-acylamino group in the 3-position.

In some embodiments, it may be found that the presence of this tri-substituted nitrogen atom leads to a bathochromic dye hue shift in the absorption curve of the azamethine dye formed as the condensation product of an oxidized arylamine developer with a coupler of formula (I) in accordance with the present invention. Accordingly, at least one of R, $R_1$ and $R_2$ may include a dye hue-shifting group which in the dye causes a hypsochromic dye hue shift to counteract the bathocromic hue shift as a result of the above tri-substitution. The dye hue-shifting group will be selected such that the net shift is such that the coupler is suitable for use as a magenta coupler forming a dye with a peak absorption less than 565 nm in color photographic materials.

According to a further aspect of the invention there is provided the use of an image dye-forming coupler of formula (I)' capable of forming a dye by reaction with oxidized color developing agent in a photographic material, comprising a support bearing a light-sensitive silver halide emulsion layer in association with the coupler, to provide an image of enhanced stability to exposure to light, wherein the coupler has the formula:

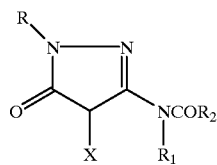

I wherein X is H or a coupling-off group, R is H; or R, $R_1$ and $R_2$ are the same or different and are coupler-modifying functional groups; or $R_1$ and $R_2$ taken together with the nitrogen atom and the carbonyl group form a 5–10 membered heterocyclic ring which may contain one or more further heteroatoms selected from N, O and S, said heterocyclic ring being unsubstituted or substituted with one or more coupler-modifying functional groups.

The couplers of the present invention of formulae (I) and (I)' may be used as the main image dye-forming couplers within an unprefogged photographic element. Naturally, in some embodiments, additional ancillary couplers of known kinds may be used such as, for example, masking couplers and the like.

However, the present couplers of the invention may also be used in conjunction with other main image dye-forming couplers within the element. It has been found surprisingly that even at low mole ratios of couplers of the invention dramatic improvements in light stability can be obtained.

There is further provided therefore the use of a coupler of formula (I)' in combination with another main image dye-forming coupler in a photographic material to provide an image of enhanced stability to exposure to light.

In the coupler of formulae (I) and (I)' the substituents R, $R_1$ or $R_2$ are sufficiently lipophilic, either singly or in combination, so as to render the coupler immobile in a photographic material.

In a particular embodiment, and subject to the above disclaimers for couplers of formula (I), R, $R_1$ and $R_2$ are the same or different and are selected independently from alkyl, aryl or heterocyclic each of which is unsubstituted or substituted with one or more coupler-modifying groups; or $R_1$ and $R_2$ form a ring as hereinbefore defined, such as, for example, a pyrrolidinone or indole.

Preferably R, $R_1$ and $R_2$ are selected from unsubstituted or substituted alkyl, phenyl, naphthyl, pyridyl or quinolinyl. Preferably R is phenyl, especially substituted phenyl. $R_1$ and $R_2$ are more preferably alkyl, which may or may not be substituted, or phenyl, most preferably substituted.

As used herein and throughout the specification the term alkyl refers to an unsaturated or saturated straight or branched chain alkyl group having 1–20 carbon atoms or a cyclic group having 3–8 carbon atoms in the ring.

Where R, $R_1$ or $R_2$ is substituted, the substituent(s) may be one or more groups selected independently from halogen, alkyl, aryl, heteroaryl, carboxylic acid, alkoxycarbonyl, aryloxycarbonyl, primary or secondary alkyl- or aryl-amido, alkyl- or aryl-sulfonamido, primary, secondary or tertiary amino, alkoxy, aryloxy, acyloxy, alkyl- or aryl-carbamoyl, alkyl- or aryl-sulfamoyl, alkyl- or aryl-sulfonyl or alkyl- or aryl-sulfonyloxy. It will be appreciated of course that these substituent groups may themselves be unsubstituted or substituted with one or more groups selected from the above list, e.g. trifluoroalkyl, which may themselves be further substituted.

As mentioned above R, $R_1$ and/or $R_2$ may be selected to include an hypsochromic dye hue-shifting group. To this end one or more of R, $R_1$ and $R_2$ may be a substituted aryl group which includes at least one electron-donating substituent; typically the substituted aryl group may include one or more of alkoxy (e.g. methoxy), alkyl (e.g. methyl) and amino (e.g. dimethylamino).

In a preferred aspect of the present invention, said coupler may have the following structure (II):

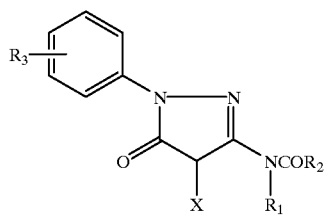

II wherein $R_3$ is H or one to five coupler-modifying functional groups, which may be the same or different, and X, $R_1$ and $R_2$ are as defined above for formula (I).

In some embodiments $R_3$ of formula (II) may represent at least one electron-donating group to provide a hypsochromic dye hue-shifting effect as described above. Said electron-donating group(s) may be positioned in the ortho- or para-positions, and may, as before, be one or more alkoxy, alkyl, alkylamido or amino.

Alternatively, where $R_3$ is not required to exert a hypsochromic dye hue-shifting effect, $R_3$ may represent one to three chloro-substituents, such that R is e.g. trichlorophenyl.

It will be appreciated that X may be H such that the image dye-forming couplers of the present invention are 4-equivalent couplers. Alternatively, X may be any coupling-off group known to a person skilled in the art. In some embodiments X may be selected from halo, acyloxy, sulfonyloxy, aryloxy, heteroaryloxy, alkylthio, arylthio, heteroarylthio, aminocarbonyloxy and imido. In other embodiments X may be derived from heterocyclic compounds such as pyridone, pyridazinone, triazole, triazoledione, tetrazole, imidazole, pyrazole or benzotriazole. Any of these moieties, other than halo, may be substituted with one or more substituents selected from those recited above for R, $R_1$ and $R_2$. Preferably, X will be hydrogen or unsubstituted or substituted alkylthio, arylthio, aryloxy, pyrazole or imidazole.

In a particular aspect of the invention, X may be hydrogen or a substituted or unsubstituted phenylthio such as, for example, 2-[2-(2,4-dipentylphenoxy)-butyramido]phenylthio.

In some embodiments, the coupler of the present invention may be selected from the following couplers, but these are not to be construed as limiting the scope of the invention in any way:

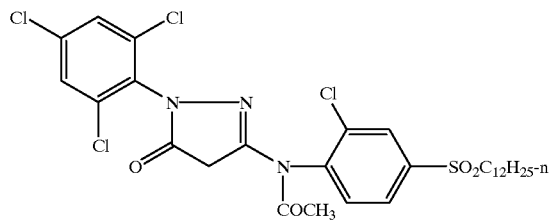

Coupler 1

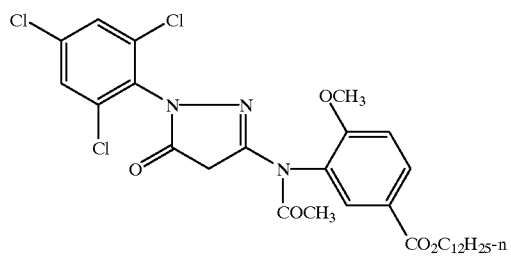

Coupler 2

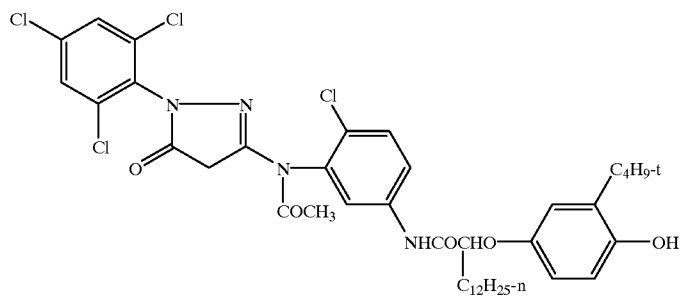

Coupler 3

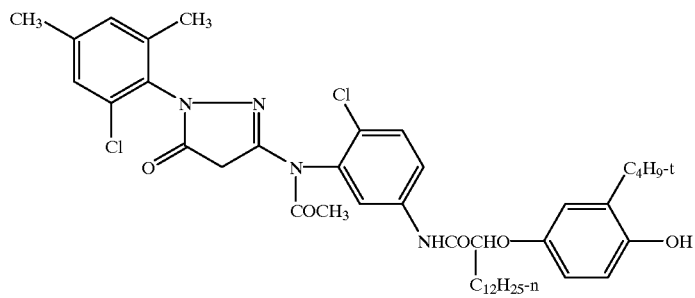

Coupler 4

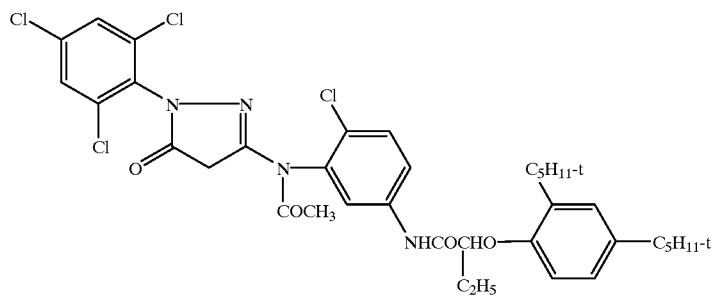

Coupler 5

-continued
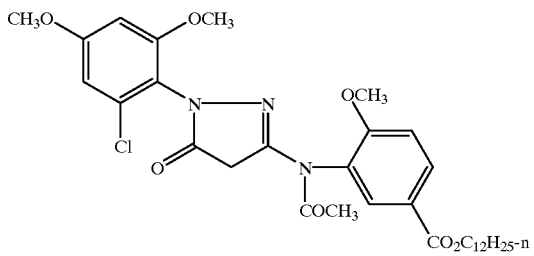
Coupler 6
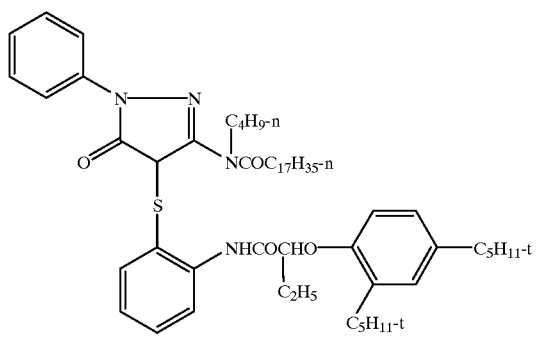
Coupler 7
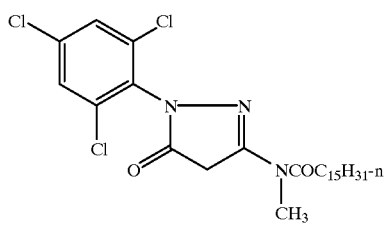
Coupler 8
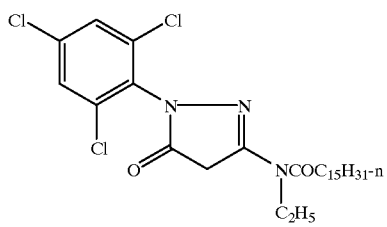
Coupler 9
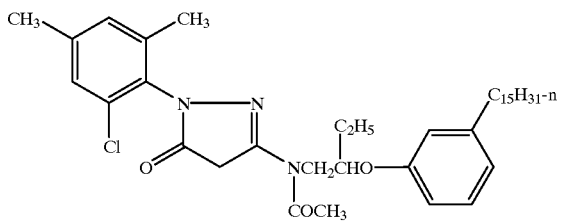
Coupler 10
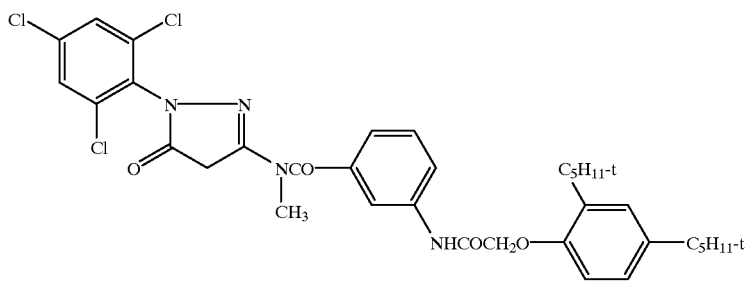
Coupler 11

Coupler 12
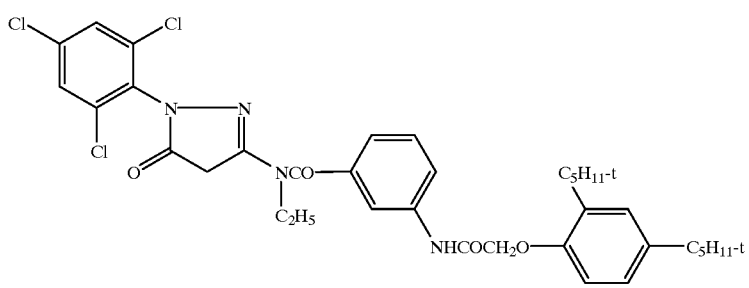
Coupler 13
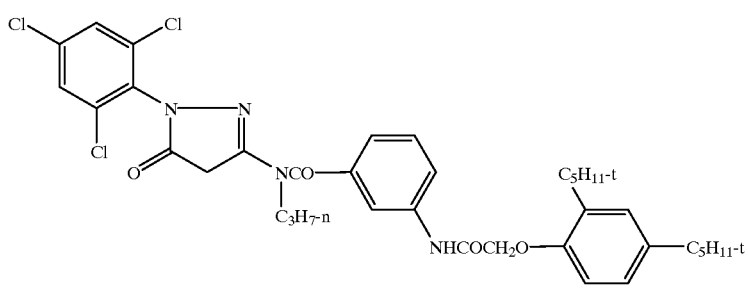
Coupler 14
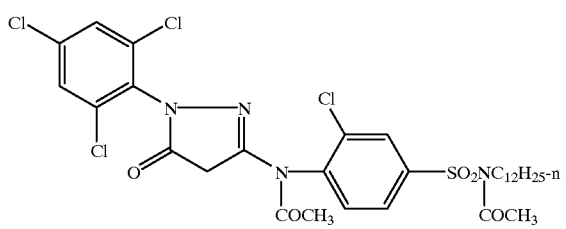
Coupler 15
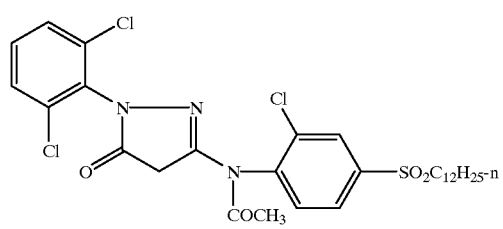
Coupler 16
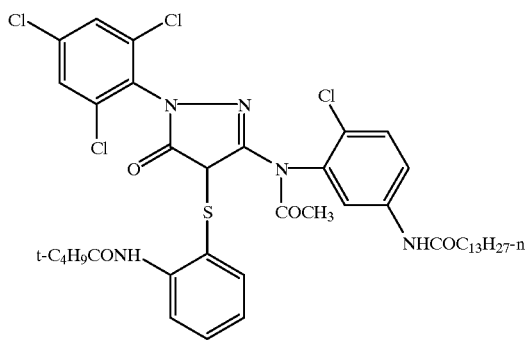

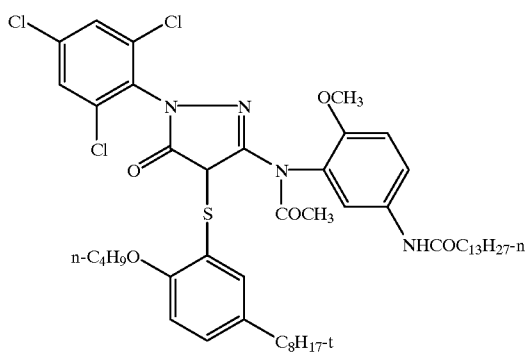
Coupler 17
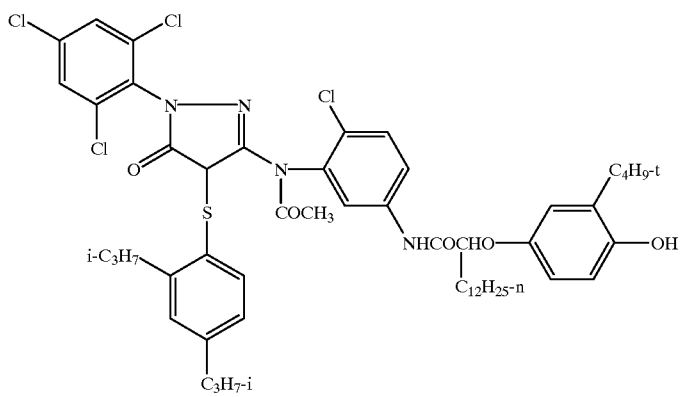
Coupler 18
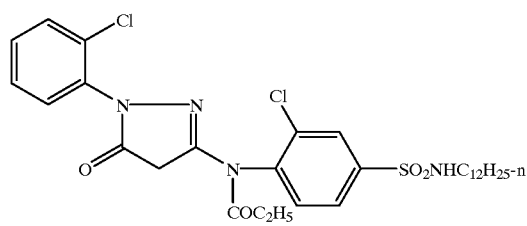
Coupler 19
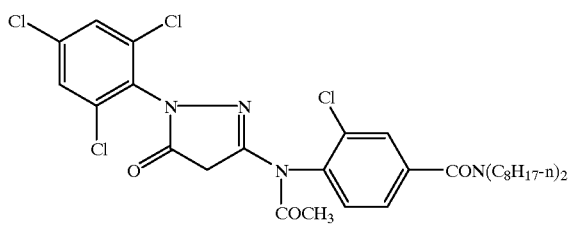
Coupler 20
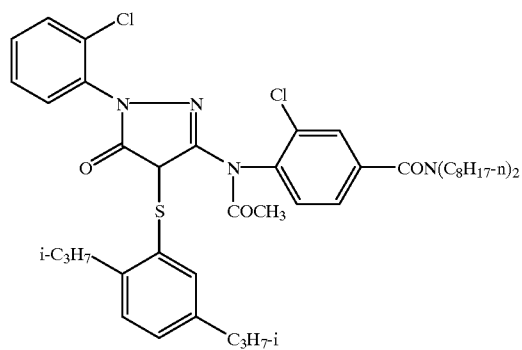
Coupler 21

-continued
Coupler 22
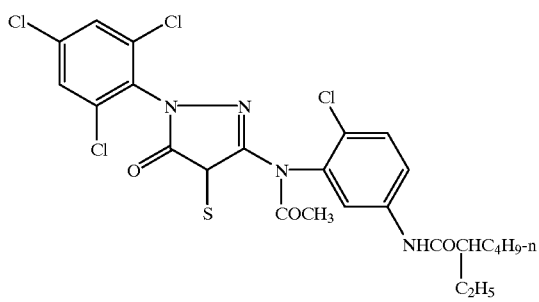
Coupler 23
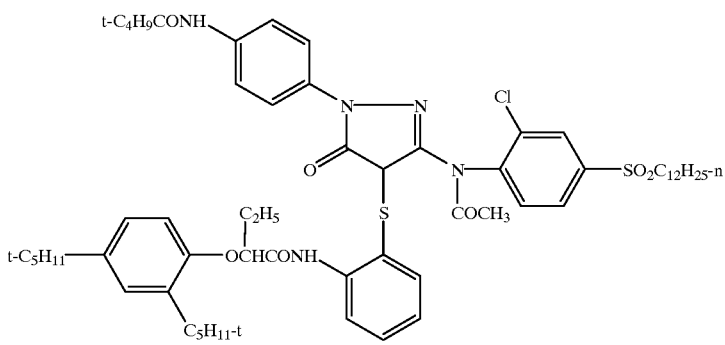
Coupler 24
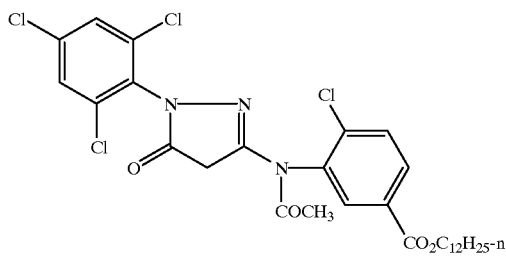
Coupler 25
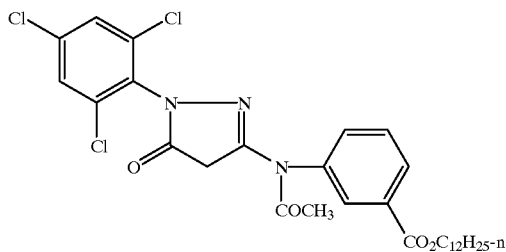
Coupler 26
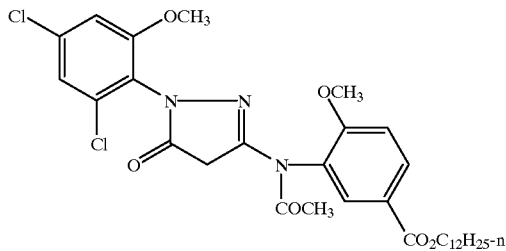

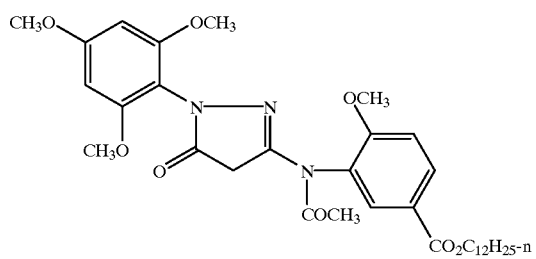
Coupler 27
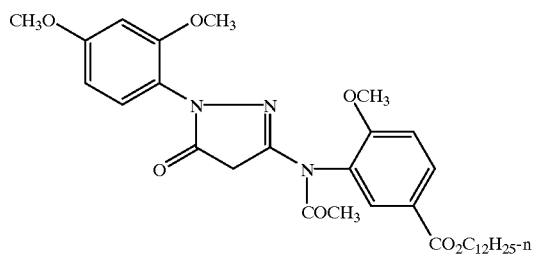
Coupler 28
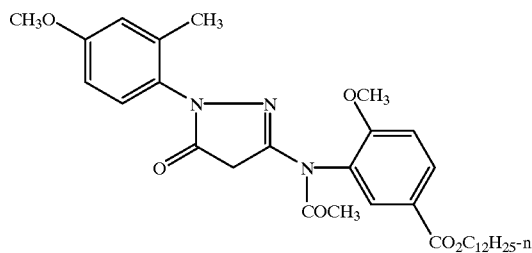
Coupler 29
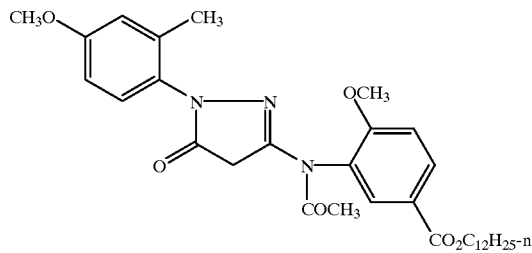
Coupler 30
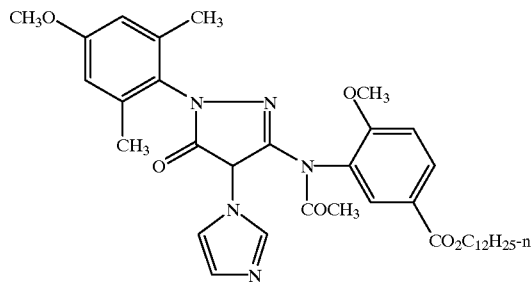
Coupler 31

Coupler 32
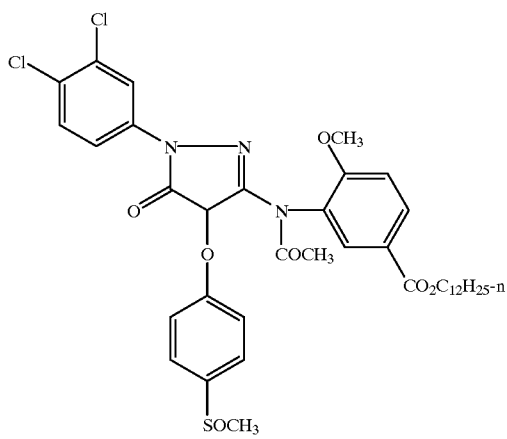
Coupler 33
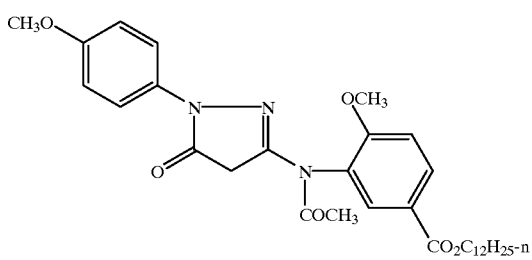
Coupler 34
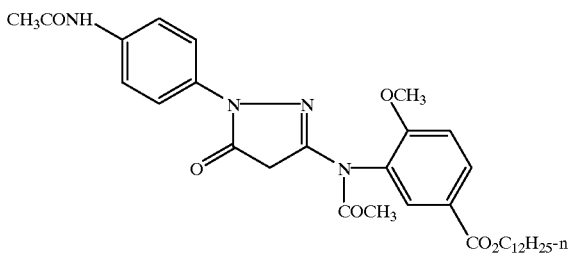
Coupler 35
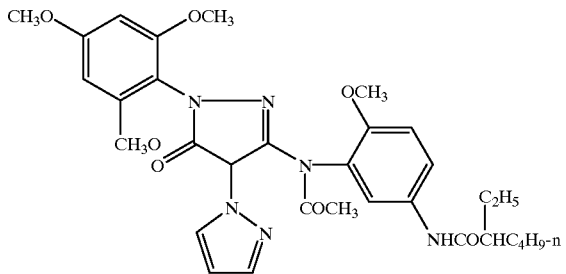

-continued
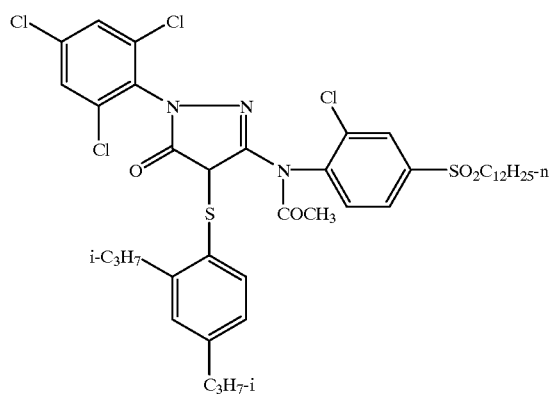
Coupler 36
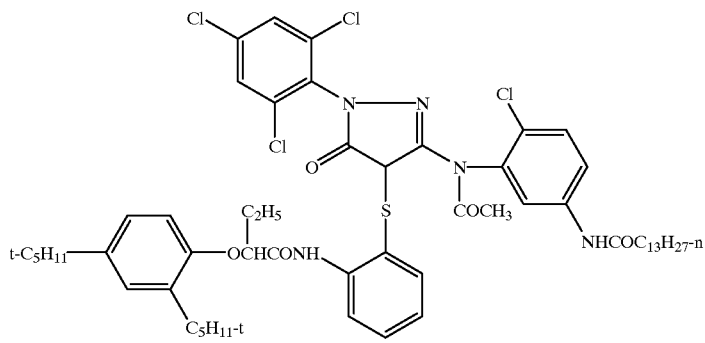
Coupler 37
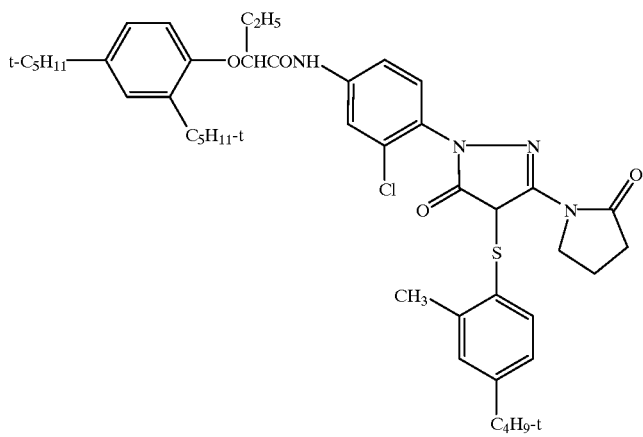
Coupler 38
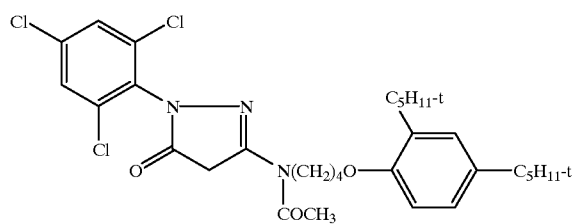
Coupler 39

-continued
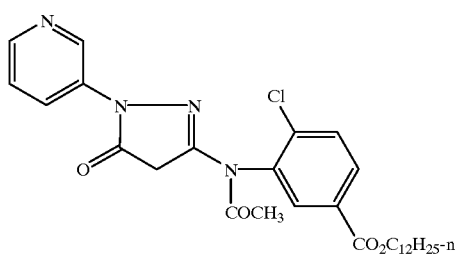
Coupler 40
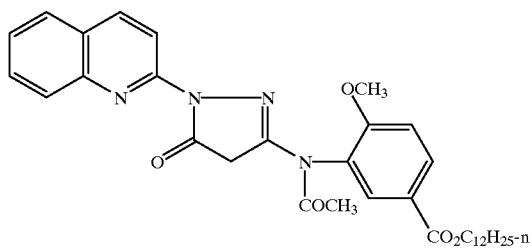
Coupler 41
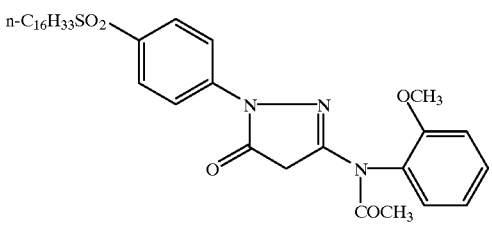
Coupler 42
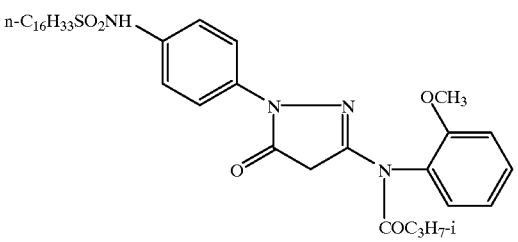
Coupler 43
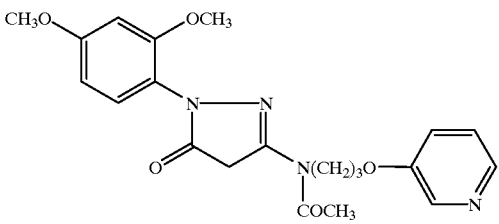
Coupler 44
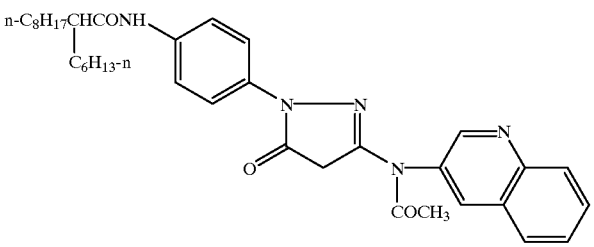
Coupler 45

Coupler 46

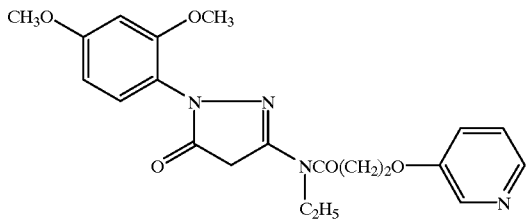

Coupler 47

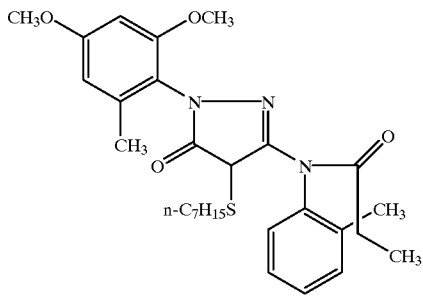

Coupler 48

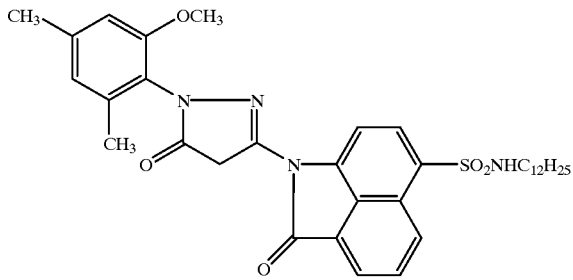

Coupler 49

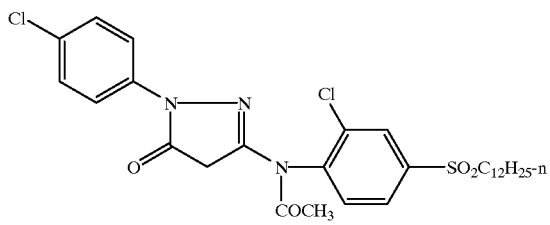

Unless otherwise specifically stated, when a substituent group contains a substitutable hydrogen, it is intended to encompass not only the substituent's unsubstituted form, but also its form further substituted with any group or groups as herein mentioned, so long as the group does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-toluylcarbonylamino, N-methylurei do, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dipersions in organic solvents, are described in Section X(E). Scan facilitating is described in Section XIV. Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895, 826, 3,002,836, 3,034,892, 3,041,236, 4,333,999, 4,883,746 and "Farbkuppler-eine Literature Ubersicht," published in Agfa Mitteilungen, Band III, pp. 156–175 (1961). Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311, 082, 2,343,703, 2,369,489, 2,600,788, 2,908,573, 3,062,653, 3,152,896, 3,519,429, 3,758,309, 4,540,654, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized color developing agent are described in such representative patents and publications as: U.S. Pat. Nos. 2,298, 443, 2,407,210, 2,875,057, 3,048,194, 3,265,506, 3,447,928, 4,022,620, 4,443,536, and "Farbkuppler-eine Literature Ubersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: UK. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. Nos. 2,983,608; 4,070,191; and 4,273,861; German Applications DE 2,706,117 and DE 2,643,965; UK. Patent 1,530,272; and Japanese Application 58-113935. The masking couplers may be shifted or blocked, if desired.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389, EP 301,477; U.S. Pat. No. 4,163, 669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859, 578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543, 323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365, 346; 373,382; 376,212; 377,463; 378,236; 384,670; 396, 486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotliazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

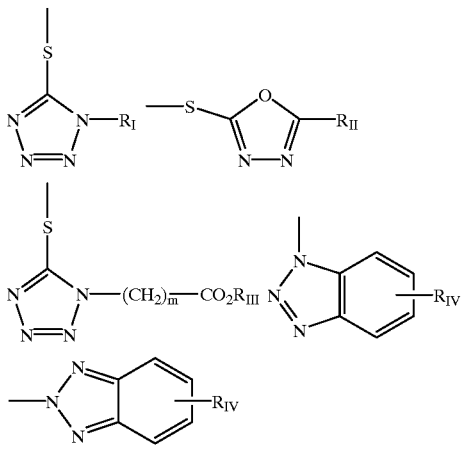

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

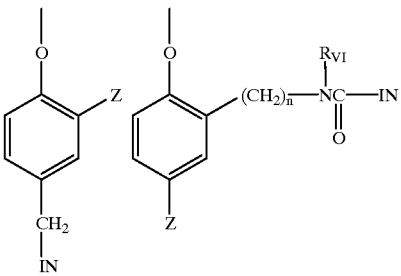

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

D1
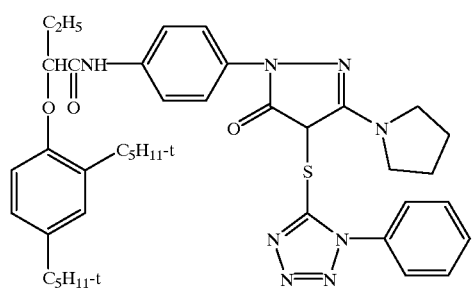
D2
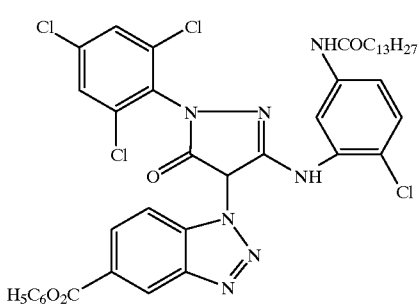
D3
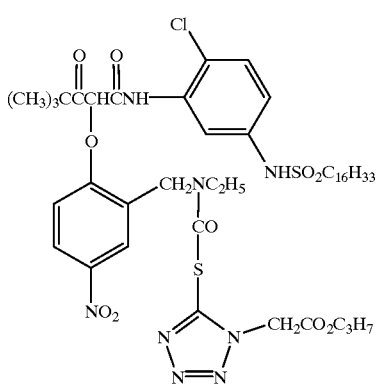
D4
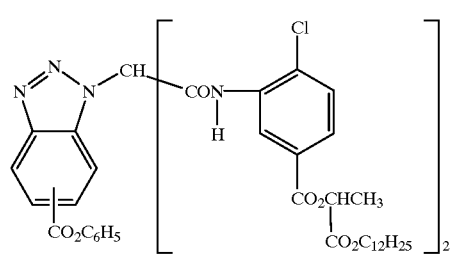
D5
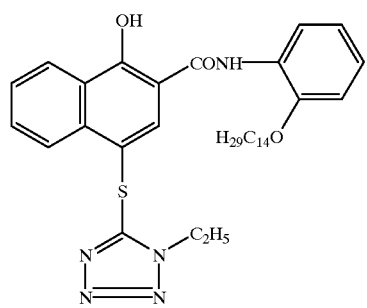
D6
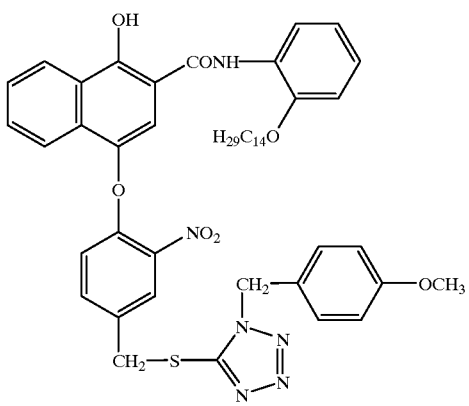
D7
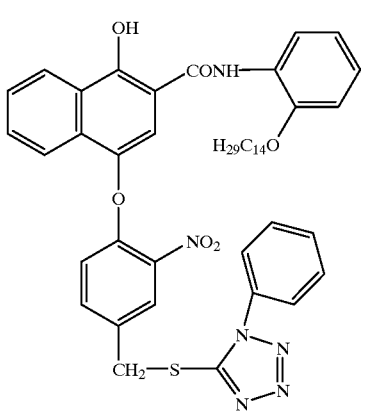
D8
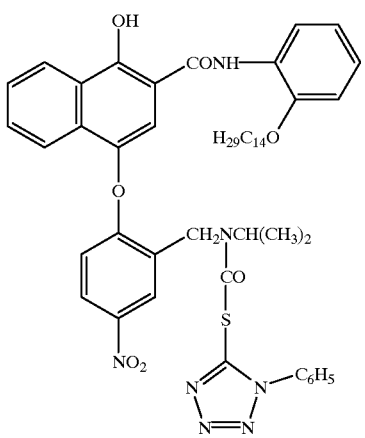

D9 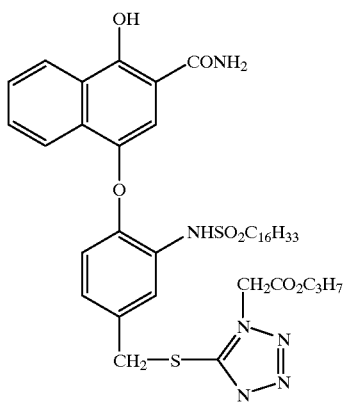

D-10 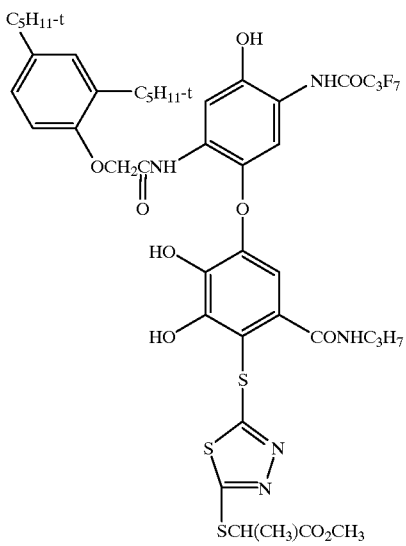

D11 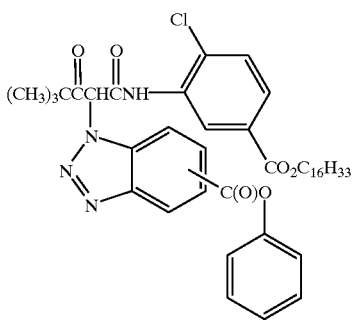

D12 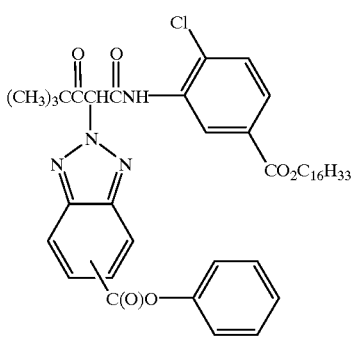

It is also contemplated that the concepts of the present invention may be employed to obtain reflection color prints as described in Research Disclosure, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where
ECD is the average equivalent circular diameter of the tabular grains in micrometers and
t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.07 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emeulsions and may be processed, for example, in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual availiable from Eastman Kodak Co. may be employed to provide the color negative image on a transparent support. Color negative development times are typically 3' 15" or less and desirably 90 or even 60 seconds or less.

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The print may then be processed to form a positive reflection image using, for example, the Kodak RA-4 process as described in The British Journal of Photography Annual of 1988, Pp 198–199. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process. Alternatively, a direct positive emulsion can be employed to obtain a positive image.

The above emulsions are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-methanesulfonamidoethyl)-N,N-diethylaniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The entire contents of the patent applications, patents and other publications referred to in this specification are incorporated herein by reference.

Following is a description by way of example only of methods of carrying the present invention into effect and is not to be construed as limiting in any way.

Pyrazolone starting materials were prepared by methods known in the art, for example as described in U.S. Pat. No. 5,411,841.

EXAMPLE 1

Preparation of Coupler 1
N-(2-Chloro-4-dodecylsulfonylphenyl)-N-[4,5-dihydro-5-oxo-1-(2,4,6-trichlorophenyl)-1H-pyrazol-3-yl]-acetamide
-(2-Chloro-4-dodecylsulfonylanilino)-4,5-dihydro-5-oxo-1-(2,4,6-trichlorophenyl)-1H-pyrazole (46.6 g, 75 mmol), (prepared as described in U.S. Pat. No. 5,411,841, column 28), was dissolved in acetyl chloride (100 ml) and acetic anhydride (75 ml) and the mixture was heated under reflux for 144 hrs. The solution was cooled then it was slowly poured into ice/water (1000 ml) and the resulting oil was extracted with ethyl acetate (2×250 ml). The combined extracts were washed with water, dried ($MgSO_4$) and evaporated to give an oil. A solution of sodium hydroxide (3.0 g, 75 mmol) in methanol (150 ml) was added to the oil and the mixture was stirred at room temperature for 1 hr. The solution was poured into 3N hydrochloric acid (500 ml), the aqueous liquor was decanted off and the residue was dissolved in ethyl acetate (250 ml). The organic solution was washed with water (100 ml), dried (MgSO$_4$) and evaporated to give an orange glass. The crude material was purified by column chromatography on 63–200 mesh silica gel eluting with a 1:3 mixture of ethyl acetate and 60–80 petroleum ether. The resulting oil was crystallized from 60–80 petroleum ether (200 ml)/ethyl acetate (40 ml) to give pure product as a white solid, 35.1 g, 71%.

$C_{29}H_{35}Cl_4N_3O_4S$ Req: C 52.5%,H 5.3%,Cl 21.4%,N 6.3%,S 4.8%; Fd: C 52.3%,H 5.15%,Cl 21.5% N 6.0%,S 4.8%

EXAMPLE 2

Preparation of Coupler 36

N-(2-Chloro-4-dodecylsulfonylphenyl)-N-[4,5-dihydro-4-(2,4-diisopropylphenylthio)-5-oxo-1-(2,4,6-trichlorophenyl)-1H-pyrazol-3-yl]acetamide Sulfuryl chloride (6.2 g, 46 mmol) was added dropwise to a stirred solution of 2,4-diisopropylthiophenol (8.9 g, 46 mmol) in dichloromethane (50 ml) and stirring was continued at room temperature for 2 hrs. Volatiles were removed by rotary evaporation to give an oil. A solution of N-(2-chloro-4-dodecylsulfonylphenyl)-N-[4,5-dihydro-5-oxo-1-(2,4,6-trichlorophenyl)-1H-pyrazol-3-yl]acetamide (29.0 g, 44 mmol) in N,N-dimethylformamide (75 ml) was added to the oil and the mixture was stirred at room temperature for 26 hrs. The solution was poured into 3N hydrochloric acid (750 ml) and the resulting sticky solid was collected by filtration. The solid was dissolved in ethyl acetate (200 ml) and the organic solution was washed with brine (100 ml), dried (MgSO$_4$) and evaporated to an orange glass. The crude material was purified by column chromatography on 63–200 mesh silica gel eluting with 1:4 ethyl acetate/60–80 petroleum ether. Pure product was obtained as a cream colored glass, 11.7 g, 31%. $C_{41}H_{51}Cl_4N_3O_4S_2$ Req: C 57.5%,H 6.0%,Cl 16.6%,N 4.9%,S 7.5%; Fd: C 57.1%,H 6.1%,Cl 16.4%,N 4.8%,S 7.2%

EXAMPLE 3

Preparation of Coupler 3

N-{4-Chloro-3-[4,5-dihydro-5-oxo-1-(2,4,6-trichlorophenyl)-1H-pyrazol-3-yl-N'-acetyl-amino]phenyl}-2-[3-(1,1-dimethylethyl)-4-hydroxyphenoxy]tetradecanamide.

N-{4-Chloro-3-[4,5-dihydro-5-oxo-1-(2,4,6-trichlorophenyl)-1H-pyrazol-3-ylamino]phenyl}-2-[3-(1,1-dimethylethyl)-4-hydroxyphenoxy]tetradecanamide (15.6 g, 20 mmol) was dissolved in acetyl chloride (60 ml) and acetic anhydride (40 ml) and heated at reflux for 3 hrs. The cooled solution was slowly added to ice/water (1000 ml) and the aqueous solution decanted off and the oily residue dissolved in ethyl acetate (200 ml). The organic solution was washed, dried (MgSO$_4$), and evaporated to give an oil. The oil was dissolved in methanol (75 ml) and to this was added sodium hydroxide (0.8 g, 20 mmol) in methanol (20 ml) and the solution stirred at room temperature for 1 hr. The solution was poured into 3N hydrochloric acid (750 ml) and the precipitate collected by filtration to give a pale pink solid. The crude material was purified by column chromatography using silica gel and 1:2 ethyl acetate: 60–80 petroleum ether to elute. The pure product was obtained as a white glass, 14.4 g, 88%.

$C_{41}H_{50}Cl_4N_4O_5$ Reqs: C 60.0%,H 6.1%,Cl 17.3%, N 6.8%; Fd: C 60.0% H 5.6%,Cl 17.1%, N 6.6%

EXAMPLE 4

Preparation of Coupler 11

N-[4,5-Dihydro-5-oxo-1-(2,4,6-trichlorophenyl)-1H-pyrazol-3-yl]-N-methyl-3-(2,4-di-t-pentylphenoxyacetamido)benzamide (a) 4,5-Dihydro-5-oxo-1-(2,4,6-trichlorophenyl)-1H-pyrazol-3-yl formamide.

Formic acid (98–100%, 33.0 g, 0.65 mol) was added dropwise to stirred acetic anhydride (54.0 g, 0.52 mol) at 0–5° C. The mixture was gently heated at 50–55° C. in an oil bath for 1.5 hr and then cooled to room temperature. Tetrahydrofuran (50 ml) was added followed by 3-amino-1-(2,4,6-trichlorophenyl)-5-pyrazolone (55.7 g, 0.20 mol) in dry tetrahydrofuran (11). The mixture was stirred for 48 hrs and the solvents removed by evaporation. The residual product was crystallized from ethyl acetate to give a yellow powder, 39.7 g, 65%.

$C_{10}H_6Cl_3N_3O_2$ Reqs: C 39.2%, H 2.0%, N 13.7%; Fd: C 39.2%, H 2.0%, N 13.5%

(b) 4,5-Dihydro-3-methylamino-5-oxo-1-(2,4,6-trichlorophenyl)-1H-pyrazole 4,5-Dihydro-5-oxo-1-(2,4,6-trichlorophenyl)-1H-pyrazol-3-yl formamide (39.6 g, 129.2 mmole) was dissolved in dry tetrahydrofuran (500 ml) with warming and then cooled to 10° C. with stirring. Borane dimethylsulfide complex (10M, 80 ml, 800 mmole) was added dropwise by syringe through a septum cap. The reaction mixture was heated on a steam bath for ca 12 hrs (overnight), cooled in an ice bath, methanol (150 ml) added dropwise and the mixture stirred for 1 hr until the effervescence had subsided. Concentrated hydrochloric acid (30 ml) was then added to give a clear solution. This was poured into water (51) and extracted with ethyl acetate (×2) and the extract washed and dried (MgSO$_4$). Evaporation of the solvent left a white glass which was dried under vacuum for 2 hrs. The yield of product was 33.4 g, 88%.

(c) N-[4,5-Dihydro-5-oxo-1-(2,4,6-trichlorophenyl)-1H-pyrazol-3-yl]-N-methyl-3-nitrobenzamide.

4,5-Dihydro-3-methylamino-5-oxo-1-(2,4,6-trichlorophenyl)-1H-pyrazole (10.0 g, 34.2 mmole) was dissolved in a mixture of tetrahydrofuran (75 ml) and pyridine (15 ml) and cooled in an ice bath. m-Nitro-benzoyl chloride (12.7 g, 68.5 mmole) was dissolved in tetrahydrofuran (20 ml) and added dropwise to the stirred mixture. Stirring was continued for 24 hr and the mixture was then poured into stirred dilute hydrochloric acid (1.51), the oil extracted into ethyl acetate and the extract washed and dried. The solvent was removed by evaporation and replaced with ethanol (100 ml). A solution of sodium hydroxide (6.8 g, 170 mmole) in water (20 ml) was added dropwise and the mixture stirred for 1 hr. The oil gradually dissolved and a solid gradually formed. The mixture was poured into dilute hydrochloric acid (11) and the oil extracted into ethyl acetate, washed with sodium bicarbonate solution, water and then dried. The solvent was removed by evaporation and the residue chromatographed on silica gel using ethyl acetate as eluent to give the product as a slightly pink glass, 9.1 g, 60%

$C_{17}H_{11}Cl_3N_4O_4$ Reqs: C 46.2%, H 2.5%, N 12.7%; Fd: C 46.3%, H 2.7%, N 12.9%

(d) N-[4,5-Dihydro-5-oxo-1-(2,4,6-trichlorophenyl)-1H-pyrazol-3-yl]-N-methyl-3-aminobenzamide.

N-[4,5-Dihydro-5-oxo-1-(2,4,6-trichlorophenyl)-1H-pyrazol-3-yl]-N-methyl-3-nitrobenzamide (8.8 g, 19.9 mmole) was dissolved in acetic acid (200 ml) and 10% palladium on charcoal catalyst (0.8 g) added. The mixture was hydrogenated under pressure (30 atms) for 4 hr, the catalyst removed by filtration through Kieselguhr, and the solvent removed by evaporation. The product was dried under vacuum to give a white glass, 8.2 g, 100%.

(e) N-[4,5-Dihydro-5-oxo-1-(2,4,6-trichlorophenyl)-1H-pyrazol-3-yl]-N-methyl-3-(2,4-di-t-pentylphenoxyacetamido)benzamide (Coupler 11).

N-[4,5-Dihydro-5-oxo-1-(2,4,6-trichlorophenyl)-1H-pyrazol-3-yl]-N-methyl-3-aminobenzamide (8.2 g, 19.9 mmole) was dissolved in a mixture of tetrahydrofuran (100 ml) and pyridine (20 ml) and cooled in an ice bath. 2,4-Di-t-pentylphenoxyacetyl chloride (20.5 mmole) was dissolved in tetrahydrofuran (20 ml) and added dropwise to the stirred mixture. Stirring was continued for 1 hr and the mixture was then poured into stirred dilute hydrochloric acid (1.51), the oil extracted into ethyl acetate and the extract washed and dried. The solvent was removed by evaporation and replaced with ethanol (100 ml). A solution of sodium hydroxide (0.8 g, 20 mmole) in water (5 ml) was added dropwise and the mixture stirred for 15 min. The oil gradually dissolved and a solid gradually formed. The mixture was poured into dilute hydrochloric acid (11) and the pale orange solid filtered off washed and dried. The solid was chromatographed on silica gel using 1:1 60–80 petroleum ether: ethyl acetate as eluent to give the product as a white glass, 6.9 g, 50%.

$C_{35}H_{39}Cl_3N_4O_4$ Reqs: C 61.3%, H 5.7%, N 8.2%; Fd: C 61.0%, H 5.8%, N 7.9%

EXAMPLE 5

Preparation of Coupler 10
N-[1-(2-Chloro-4,6-dimethylphenyl)-4,5-dihydro-5-oxo-1H-pyrazol-3-yl]-N-{1-[2-(3-n-pentadecylphenoxy)-butyl]}acetamide (a) 1-(2-Chloro-4,6-dimethylphenyl)-4,5-dihydro-5-oxo-3-{1-[2-(3-n-pentadecylphenoxy)butyl]amino}-1H-pyrazole N-[1-(2-Chloro-4,6-dimethylphenyl)-4,5-dihydro-5-oxo-1H-pyrazol-3-yl]-2-(3-n-pentadecylphenoxy)butanamide (12.2 g, 20 mmole) was stirred in tetrahydrofuran (200 ml) and cooled to 10° C. in an ice bath. Borane dimethylsulfide complex (10M, 490 mmole, 49 ml) was added dropwise by syringe through a septum cap then gradually warmed to 65° C. on a steam bath and refluxed for 3 hrs. The reaction mixture was cooled and methanol (50 ml) added dropwise with stirring. After most of the effervescence had subsided concentrated hydrochloric acid (105 ml) was added and stirring continued for 1 hr. Water was added, the mixture extracted with ethyl acetate, and the extract washed and dried. After removal of the solvent by evaporation the product was purified by column chromatography using silica gel and 1:1 ethyl acetate: 60–80 petroleum ether to elute. A beige viscous oil (10.8 g) was obtained which was used as such in the next step.

(b) N-[1-(2-Chloro-4,6-dimethylphenyl)-4,5-dihydro-5-oxo-1H-pyrazol-3-yl]-N-{1-[2-(3-n-pentadecyl-phenoxy)butyl]}acetamide (Coupler 10).

1-(2-Chloro-4,6-dimethylphenyl)-4,5-dihydro-5-oxo-3-{1-[2-(3-n-pentadecylphenoxy)butyl]amino}-1H-pyrazole (10.7 g, 18.0 mmole) and acetic anhydride (50 ml) were heated together at reflux for 15 minutes and the excess of acetic anhydride removed by evaporation. The oil was dissolved in ethyl acetate, washed with water and dried. The solvent was removed by rotary evaporation and replaced with ethanol (100 ml). A solution of sodium hydroxide (3.6 g, 90 mmole) in the minimum of water was added and stirred for 1 hr. The mixture was then added to a stirred solution of dilute (1N) hydrochloric acid (21) and the oil extracted into ethyl acetate and the extract washed and dried. The solvent was removed and the crude material purified by column chromatography using silica gel and 1:3 ethyl acetate: 60–80 petroleum ether as eluent. The pure product was obtained as a colorless glass, 4.2 g, 37%.

$C_{38}H_{56}ClN_3O_3$ Reqs: C 71.5%, H 8.8%, N 6.6%; Fd: C 71.3%, H 8.9%, N 6.4%

EXAMPLE 6

Preparation of Coupler 30
Dodecyl 3-{N-[1-(2-chloro-2,4-dimethylphenyl)-4,5-dihydro-5-oxo-1H-pyrazol-3-yl]-N-acetylamino}-4-methoxybenzoate Dodecyl 3-{N-[1-(2-chloro-2,4-dimethylphenyl)-4,5-dihydro-5-oxo-1H-pyrazol-3-yl]-amino}-4-methoxy-benzoate (10.5 g, 18.9 mmol) was dissolved in acetyl chloride (50 ml) and acetic anhydride (35 ml) and the solution was heated under reflux for 1.5 hrs. The solution was cooled, then it was slowly poured into ice/water (750 ml) and the resulting sticky solid was extracted with ethyl acetate (2×100 ml). The combined extracts were dried ($MgSO_4$) and evaporated to give an oil. Sodium hydroxide (0.8 g, 18.9 mmol) was added to a solution of the oil in methanol (80 ml) and the mixture was stirred at room temperature for 4 hrs. The solution was poured slowly into 3N hydrochloric acid (500 ml), the aqueous liquor was decanted off and the residue was dissolved in ethyl acetate (100 ml). The organic solution was dried ($MgSO_4$) and evaporated to give a glass. The crude material was recrystallized from methanol (50 ml) to give pure product as a white solid, 5.8 g, 51%.

$C_{33}H_{44}ClN_3O_5$ Req: C 66.26%, H 7.41%, N 7.03%; Fd: C 66.20%, H 7.42%, N 7.01%,

EXAMPLE 7

Preparation of Coupler 4
N-{4-Chloro-3-[4,5-dihydro-5-oxo-1-(2-chloro-4,6-dimethylphenyl)-1H-pyrazol-3-yl-N'-acetylamino]-phenyl}-2-[3-(1,1-dimethylethyl)-4-hydroxy-phenoxy] tetradecanamide.

N-{4-Chloro-3-[4,5-dihydro-5-oxo-1-(2-chloro-4,6-dimethylphenyl)-1H-pyrazol-3-ylamino]phenyl}-2-[3-(1,1-dimethylethyl)-4-hydroxyphenoxy]tetradecanamide (14.7 g, 20 mmol) was dissolved in acetyl chloride (60 ml) and acetic anhydride (40 ml) and the solution was heated under reflux for 2.5 hrs. The cooled solution was slowly added to ice/water (1000 ml), then the aqueous solution was decanted off and the oily residue was dissolved in ethyl acetate (200 ml). The organic solution was washed with water (100 ml), dried ($MgSO_4$), and evaporated to give an orange oil. The oil was dissolved in methanol (75 ml) and to this was added a solution of sodium hydroxide (0.8 g, 20 mmol) in methanol (20 ml). The resulting solution was stirred at room temperature for 1.5 hrs, then it was poured into 3N hydrochloric acid (750 ml). The resulting precipitate was collected by filtration to give a pale peach colored solid. The crude material was purified by column chromatography on silica gel eluting with a 1:3 mixture of ethyl acetate and 60–80 petroleum ether. The resulting product was dissolved in methanol (50 ml) and the solution was added slowly to water (500 ml). The product was obtained as a pale yellow solid, 12.4 g, 79%.

$C_{43}H_{56}Cl_2N_4O_5$ Reqs: C 66.2%, H 7.2%, Cl 9.1%, N 7.2%; Fd: C 65.5% H 7.1%, Cl 9.1%, N 6.95%

EXAMPLE 8

Preparation of Coupler 13
N-[4,5-Dihydro-5-oxo-1-(2,4,6-trichlorophenyl)-1H-pyrazol-3-yl]-N-propyl-3(2,4-di-t-pentyl-phenoxyacetamido)benzamide (a) 4,5-Dihydro-5-oxo-1-(2,4,6-trichlorophenyl)-1H-pyrazol-3-yl propionamide 3-Amino-1-(2,4,6-trichlorophenyl)-5-pyrazolone (35.0 g, 125 mmole) was dissolved in dry tetrahydrofuran (350 ml) and pyridine (35 ml) and the solution was cooled in an ice-bath to 10° C. A solution of propionyl chloride (35.15 g, 0.18 mmole) in tetrahydrofuran (60 ml) was added dropwise keeping the temperature below 10° C. The mixture was stirred at room temperature for 48 hrs then it was poured into dilute hydrochloric acid (2.51). The resulting gum was extracted with ethyl acetate (700 ml) and the solution was washed with water and dried ($MgSO_4$). Evaporation of the solvent under reduced pressure gave a light brown oil which was dissolved in methanol (120 ml). A solution of potassium hydroxide (70.0 g, 125 mmol) in methanol was added dropwise with stirring and the mixture was stirred for 0.5 hrs. Glacial acetic acid was added to the suspension and stirred for 2 hr. The buff colored solid was filtered off, washed with water and dried in a vacuum oven. The yield of product was 35.54 g, 85%.

$C_{12}H_{10}Cl_3N_3O_2$ Req: C 43.1%, H 3.0%, N 12.6%; Fd: C 42.8%, H 2.8%, N 12.3%

(b) 4,5-Dihydro-3-propylamino-5-oxo-1-(2,4,6-trichlorophenyl)-1H-pyrazole 4,5-Dihydro-5-oxo-1-(2,4,6-trichlorophenyl)-1H-pyrazol-3-yl propionamide (31.93 g, 95.6 mmol) was dissolved in dry tetrahydrofuran (400 ml) with warming and the solution was cooled to 10° C. with stirring. Borane dimethylsulfide complex (10M, 32 ml, 320 mmole) was added dropwise by syringe through a septum cap. The reaction mixture was heated on a steam-bath for 12 hrs then it was cooled in an ice-bath. Methanol (32 ml) was added dropwise and the mixture was stirred for 1 hr until the effervescence had subsided. Concentrated hydrochloric acid (7 ml) was added to give a clear solution. This was poured into water (100 ml) and the mixture was extracted twice with ethyl acetate (100 ml). The extracts were combined, washed with water and dried ($MgSO_4$). Evaporation of the solvent left a yellow oil which was dried under vacuum for 2 hrs. The crude product (37.1 g) was purified by column chromatography on silica gel, eluting with a 2:1 mixture of ethyl acetate and 60–80 petroleum ether to give a pale yellow oil which solidified on standing, 22.0 g, 72%.

$C_{12}H_{12}Cl_3N_3O$ Req: C 44.95%, H 3.8%, N 13.1%; Fd: C 44.75%, H 3.8%, N 12.8%

(c) N-[4,5-Dihydro-5-oxo-1-(2,4,6-trichlorophenyl)-1H-pyrazol-3-yl]-N-propyl-3-nitrobenzamide 4,5-Dihydro-3-propylamino-5-oxo-1-(2,4,6-trichlorophenyl)-1H-pyrazole (21.9 g, 68.3 mmol) was dissolved in a mixture of tetrahydrofuran (170 ml) and pyridine (34 ml) and the solution was cooled in an ice-bath. m-Nitrobenzoyl chloride (25.35 g, 136.7 mmol) was dissolved in tetrahydrofuran (40 ml) and the solution was added dropwise to the stirred, cooled mixture. Stirring was continued at room temperature for 19 hrs. A further quantity of m-nitrobenzoyl chloride (10%) was added and the mixture was stirred for 2 hrs to complete the reaction. The mixture was poured into dilute hydrochloric acid (31) and the oily solid was extracted with ethyl acetate. The extract was washed with water and dried ($MgSO_4$). The solvent was removed by evaporation and replaced with ethanol (300 ml). A solution of sodium hydroxide (13.7 g, 324 mmol) in water (40 ml) was added dropwise and the mixture was stirred for 1 hr. The mixture was poured into dilute hydrochloric acid (21) and the resulting oil was extracted with ethyl acetate. The extract was washed with water and dried ($MgSO_4$). The solvent was evaporated under reduced pressure to give a resin, 33.0 g, ca 100%. This was used in the next stage without purification.

(d) N-[4,5-Dihydro-5-oxo-1-(2,4,6-trichlorophenyl)-1H-pyrazol-3-yl]-N-propyl-3-aminobenzamide N-[4,5-Dihydro-5-oxo-1-(2,4,6-trichlorophenyl)-1H-pyrazol-3-yl]-N-propyl-3-nitrobenzamide (33.0 g, 68.3 mmol) was dissolved in glacial acetic acid (300 ml) and 10% palladium on charcoal (3.2 g) was added. The mixture was hydrogenated under pressure (30 atms) for 4 hrs, then the catalyst was removed by filtration through Kieselguhr. The solvent was removed by evaporation and the product was dried under vacuum to give a white glass, 32.5 g, ca 100%. The product was used in the next stage without purification.

(e) N-[4,5-Dihydro-5-oxo-1-(2,4,6-trichlorophenyl)-1H-pyrazol-3-yl]-N-propyl-3-(2,4-di-t-pentyl-phenoxyacetamido)benzamide(coupler 13)

N-[4,5-Dihydro-5-oxo-1-(2,4,6-trichlorophenyl)-1H-pyrazol-3-yl]-N-propyl-3-aminobenzamide (32.5 g, 68.3 mmol) was dissolved in a mixture of tetrahydrofuran (350 ml) and pyridine (35 ml) and the solution was cooled in an ice-bath. 2,4-Di-t-pentylphenoxyacetyl chloride (75.2 mmol) was dissolved in tetrahydrofuran (50 ml) and this solution was added dropwise to the stirred, cooled mixture. Stirring was continued for 1 hr then the mixture was poured into dilute hydrochloric acid (31) The resulting oil was extracted with ethyl acetate and the extract was washed with water and dried ($MgSO_4$). The solvent was evaporated under reduced pressure and replaced with ethanol (300 ml). A solution of sodium hydroxide (2.7 g, 68.3 mmol) in water (15 ml) was added dropwise and the mixture was stirred for 1 hr. The oil gradually dissolved and a solid formed. The mixture was poured into dilute hydrochloric acid (31) and the pale orange solid was filtered off, washed with water and dried. The solid was purified by column chromatography on silica eluting with a 1:1 mixture of ethyl acetate and 60–80 petroleum ether to give the product as a pale pink glass, 39.4 g, 81%. $C_{37}H_{43}Cl_3N_4O_4$ Req: C 62.2%, H 6.1%, N 7.85%; Fd: C 62.4%, H 5.8%, N 7.8%

PHOTOGRAPHIC EVALUATION OF MAGENTA COUPLERS(A)

Compounds of the present invention (and control compounds) were dispersed in coupler solvent and incorporated into photographic coatings containing a silver bromoiodide emulsion, on a transparent support, according to the following coating format:

| | | |
|---|---|---|
| Gel Supercoat | Gelatin | 1.00 g/m$^2$ |
| Emulsion Layer | Silver bromoiodide | 1.61 g/m$^2$ |
| | Coupler | 1.042 mmol/m$^2$ |
| | Gelatin | 2.42 g/m$^2$ |
| | Bis(vinylsulfonyl)methane (hardener) | 0.06 g/m$^2$ |
| Support | Cellulose acetate | |

Aqueous dispersions of the couplers were prepared by methods known in the art. The magenta dye-forming coupler dispersions contained 6% by weight of gelatin, 8.8% by weight of coupler and a 1.0:0.5:1.5 weight ratio of coupler to tricresyl phosphate coupler solvent to 2-(2-butoxyethoxy) ethyl acetate auxiliary solvent. The auxiliary solvent was included to aid in dispersion preparation and was removed by washing the dispersion for 6 hours at 4° C. and pH 6.0.

The experimental photographic coatings prepared in this way were slit and chopped into 30 cm×35 mm test strips.

After hardening the strips were exposed (0.1 sec) through a 0–0.9 ND step-wedge (0.3 ND increments) and Daylight V and Wratten 9 filters and the correct ND filters to give an optical density of about 1.0. The strips were then processed through a standard C-41 process as described in the British Journal of Photography Annual (1988), pp96–198 using the following steps and process times:

| | |
|---|---|
| Cellulose acetate | 2.5 minutes |
| Bleach | 4.0 minutes |
| Wash | 2.0 minutes |
| Fix | 4.0 minutes |
| Wash | 2.0 minutes |

Samples were cut from the magenta dye image step with density closest to 1.0. Visible absorption spectra of the resultant magenta dyes were obtained using a Pye-Unicam SP8-100 spectrophotometer. The dye sample patches, protected with a Wratten 2B gelatin filter, were faded for a period of 200 hours accumulated fade using a fadeometer in which the samples were mounted at a fixed distance of 4.0 cm from a pair of 85 W, 6 ft long color matching fluorescent tubes maintained in strictly controlled conditions of 17° C. and 50% relative humidity.

The spectrophotometric curves were remeasured after each fade period and the degree of fade quoted as the fractional decrease in density at the wavelength of maximum absorption ($\lambda$max) relative to the initial density prior to fading.

The results of the testing described above are set out in the following table:

TABLE 1

Dye Hue and Light fade data (a) Compounds of formula (I)

| COUPLER | $\lambda$max (nm) | % DYE LIGHT FADE |
|---|---|---|
| COUPLER 7 | 553.5 | 12 |
| COUPLER 8 | 564.5 | 5 |
| COUPLER 9 | 563.5 | 5 |
| COUPLER 10 | 558.5 | 6 |
| COUPLER 13 | 564.0 | 11 |
| COUPLER 26 | 561.5 | 8 |
| COUPLER 30 | 562.0 | 7 |
| CONTROL 1 | 556.0 | 47 |
| CONTROL 2 | 547.5 | 67 |
| CONTROL 3 | 547.0 | 43 |
| CONTROL 4 | 553.5 | 82 |
| CONTROL 5 | 551.5 | 32 |

(b) Compounds of formula (I)'

| COUPLER | | % Dye Light Fade |
|---|---|---|
| COUPLER 1 | 577.0 | 7 |
| COUPLER 2 | 569.0 | 0 |
| COUPLER 3 | 572.5 | 6 |
| COUPLER 5 | 571.5 | 8 |
| COUPLER 11 | 567.5 | 12 |
| COUPLER 12 | 566.5 | 11 |
| COUPLER 14 | 576.5 | 4 |
| COUPLER 22 | 570.0 | 8 |
| COUPLER 24 | 573.5 | 4 |
| COUPLER 39 | 566.0 | 7 |

The chemical structures of controls 1, 2, 3, 4 and 5 are as follows:

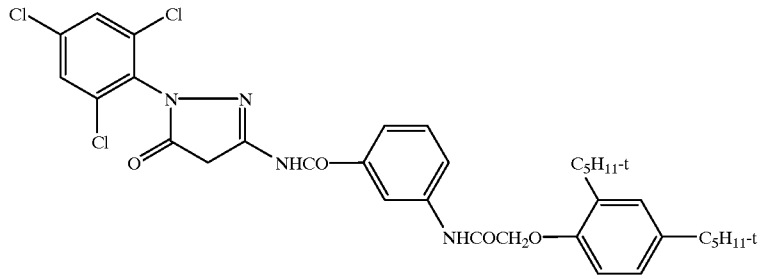

Control 1

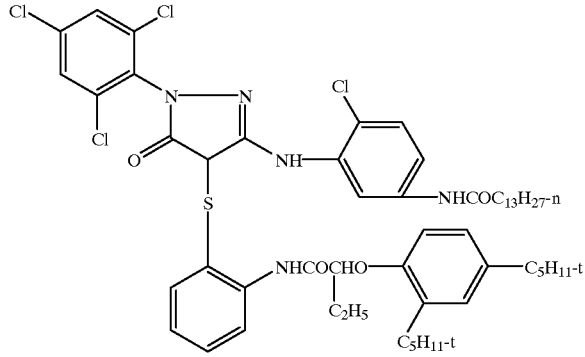

Control 2

-continued

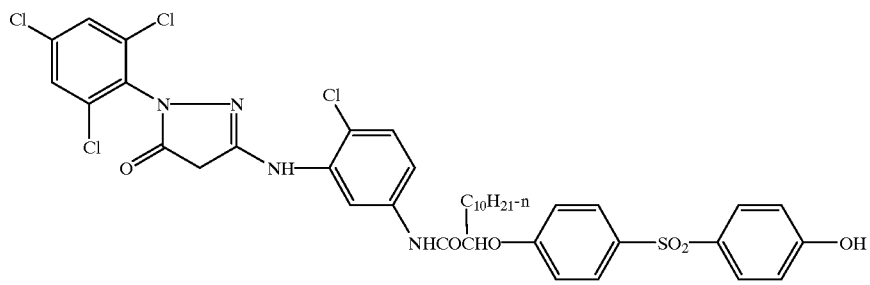

Control 3

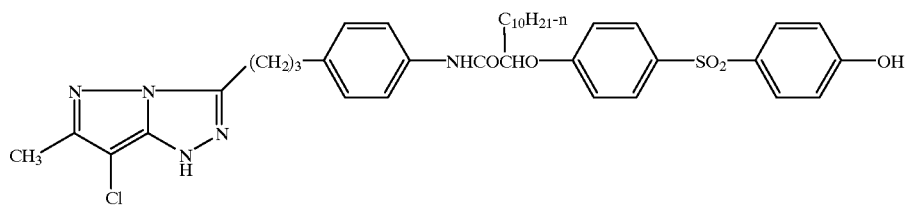

Control 4

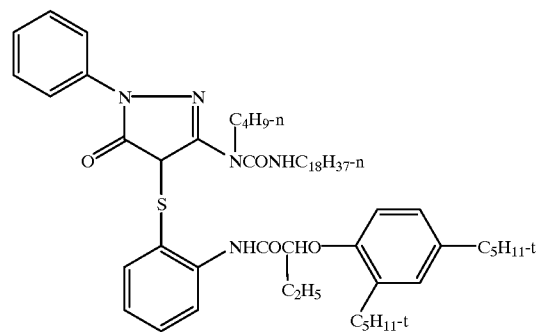

Control 5

PHOTOGRAPHIC EVALUATION OF MAGENTA COUPLERS (B)

Compounds of the present invention (and control compounds) were dispersed in coupler solvent and additionally incorporated into photographic coatings according to the following coating format.

| Gel Supercoat | Gelatin<br>Bis(vinylsulfonyl)<br>methylether<br>(1.75% of total gel) | 2.69 g/m² |
| --- | --- | --- |
| Emulsion Layer | Silver bromiodide<br>Coupler<br>Gelatin | 1.08 g/m²<br>0.57 mmol/m²<br>3.77 g/m² |
| Support | Cellulose acetate with<br>Rem-Jet Backing | |

Aqueous dispersions were prepared using a weight ratio of 1.0:0.8:0.2 of coupler to tricresyl phosphate coupler solvent to N,N-dibutyl-2-butoxy-5-t-octylaniline as stabilizer, except for control 1 wherein a weight ratio of 1.0:5.0 of coupler to N,N-dibutyllauramide coupler solvent was used and for control 6 wherein a weight ratio of 1.0:1.0 of coupler to tricresylphosphate coupler solvent was used. The coatings were exposed and processed as previously described. Light stability was measured as loss in maximum density using dye patches protected by a Wratten 2B gelatin filter, exposed to a 50 Klux high intensity light source for 5 days.

TABLE 2

Dye Hue and Light fade data (a) Compounds of formula (I)

| COUPLER | λmax (nm) | % DYE LIGHT FADE |
| --- | --- | --- |
| COUPLER 4 | 563 | 2.7 |
| COUPLER 7 | 555 | 8.6 |
| *COUPLER 30 | 559 | 0.3(+) |
| CONTROL 1 | 552 | 39.1 |
| CONTROL 5 | 547 | 31.4 |
| CONTROL 6 | 543 | 14.9 |
| CONTROL 7 | 536 | 18.5 |
| CONTROL 8 | 544 | 38.7 |

(b) Compounds of formula (I)'

| COUPLER | λmax (nm) | % Dye Light Fade |
| --- | --- | --- |
| *COUPLER 2 | 573 | 2.8(+) |
| COUPLER 3 | 568 | 0 |
| *COUPLER 5 | 569 | 1.2(+) |

*In these cases a slight increase in dye density was noted.

Control Couplers 6 to 8 have the following structures:

Control Coupler 6

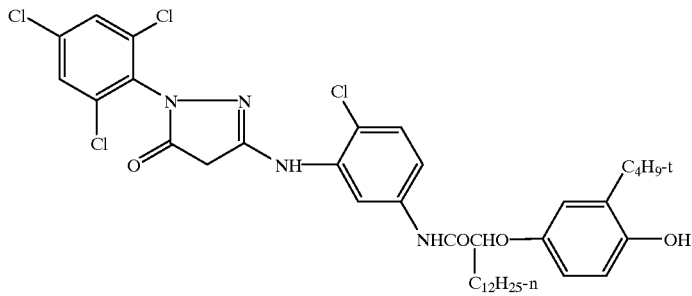

Control Coupler 7

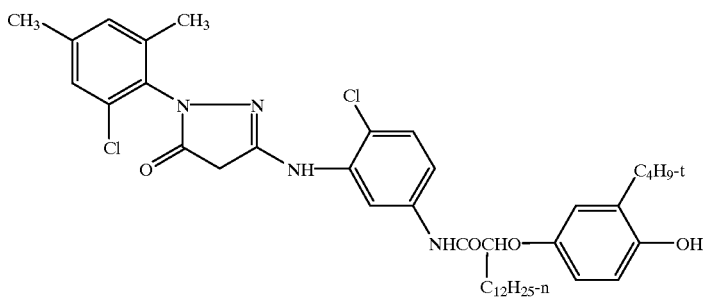

Control Coupler 8

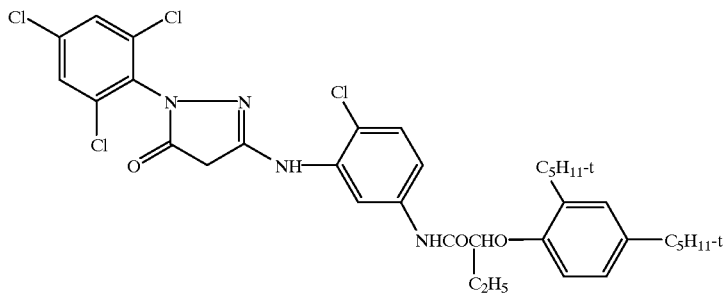

From the above, it will be seen that the couplers in accordance with the present invention as hereinbefore described are significantly more stable to exposure to actinic light as compared with the control couplers, some of which are used in commercially available photographic materials, namely controls 1, 2, 4 and 6.

From the Tables it will be seen, by way of example, that when comparing the % dye-light fades of coupler 7 and control 5 there is nearly a 3-fold (Table 1) or 4-fold (Table 2) improvement with the former. Similarly from Table 1 coupler 13 has more than a 4-fold increased light stability compared with structurally similar control 1 found in commercial photographic products. Further improvements are found in Table 2 where there is a nearly 7-fold improvement for coupler 4 compared with control 7. Coupler 3 showed no measurable decrease in light stability over 5 days compared with a nearly 15% fade of closely related control 6; also used in commercial photographic material. Even more significantly from Table 2 it will be seen that comparing the light fades of coupler 5 with structurally similar control 8, there is a dramatic, i.e. more than 30-fold, improvement in the results obtained with the coupler of the present invention.

PHOTOGRAPHIC EVALUATION OF MAGENTA COUPLERS (C)

Mixtures of compounds of the present invention and control compounds were dispersed in coupler solvent and incorporated into photographic coatings containing a silver bromoiodide emulsion, on a transparent support, according to the following coating format:

| Gel Supercoat | Gelatin | 1.00 g/m² |
|---|---|---|
| Emulsion Layer | Silver bromoiodide | 0.80 g/m² |
| | Total coupler (control coupler + coupler of invention) | 0.52 mmol/m² |
| | Gelatin | 2.42 g/m² |
| | Bis(vinylsulfonyl) methane (hardener) | 0.06 g/m² |
| Support | Cellulose acetate | |

Aqueous dispersion of the couplers were prepared by methods known in the art, as described under Evaluation (A).

The control coupler and coupler of the invention may either be dispersed separately, using the above formulation in Evaluation (A), and added to the coating melt in the correct ratio to give a total molar coupler laydown of 0.52 mmol/m² or may be co-dispersed in the same dispersion using the appropriate ratio of control coupler to coupler of the invention to give a total coupler laydown of 0.52 mmol/m².

The experimental photographic coatings prepared in this way were processed and tested for light stability as described in Evaluation (A).

Coupler 49 of the invention was coated with control coupler 2 as above, using separate dispersions of the two couplers, at a range of laydowns such that the total laydown of the two couplers was always 0.52 mmol/m².

The results of the experiment are summarized in Table 1.

TABLE 1

| % Control Coupler 2 | % Coupler 49 of the Invention | % Dye Light Fade |
|---|---|---|
| 100.0 | 0 | 79.0 |
| 94.0 | 6.0 | 54.0 |
| 87.5 | 12.5 | 36.0 |
| 75.0 | 25.0 | 24.0 |
| 62.5 | 37.5 | 19.0 |
| 50.0 | 50.0 | 16.0 |
| 0 | 100.0 | 13.0 |

It can be seen that addition of coupler 49 dramatically improved the light stability of the control coupler 2. Control coupler 2 with no added coupler 49 showed a fade of 79% from its initial density position after 200 hour fade. Even a small amount of this coupler gave a large improvement such that with an addition of as little as 6% a fade of 54% was achieved.

The fade results are shown graphically in the Figure (represented by the solid curve). The dashed straight line represents the fade which would be expected from mixtures of coupler 49 and control coupler 2 if the improvement in fade were merely an additive effect. It can be clearly seen from the solid curve that the magnitude of the improvement in light stability obtained by the use of coupler 49 was unexpected, representing a synergistic effect resulting from use of the two couplers in combination. In particular it will be noted that most of the improvement in light stability was achieved with a molar ratio of less than 30% of coupler 49.

What is claimed is:

1. A photographic element comprising a silver halide emulsion layer having associated therewith an image dye-forming coupler of formula (I):

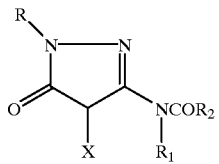

I wherein X is H or a coupling-off group, R is H or a coupler modifying group; $R_1$ and $R_2$ are the same or different and are coupler-modifying functional groups selected independently from alkyl, aryl or heterocyclic, each of which is unsubstituted or substituted with one or more coupler-modifying functional groups; or $R_1$ and $R_2$ taken together with the nitrogen atom and the carbonyl group form a 5–10 membered heterocyclic ring which may contain one or more further heteroatoms selected from N, O and S, said heterocyclic ring being unsubstituted or substituted with one or more coupler-modifying functional groups (with the provisos that (a) the moiety $N(R_1)COR_2$ may not be a carbamate, ureido or imido and (b) $R_1$ and $R_2$ may not both be phenyl or substituted phenyl); provided that $R_1$ and $R_2$ taken together with the nitrogen atom and the carbonyl group may form a 5–10 membered heterocyclic ring which may contain one or more further heteroatoms selected from N, O and S, said heterocyclic ring being unsubstituted or substituted with one or more coupler-modifying functional groups with the further proviso that the ring is not a cyclic carbonate, ureido or imido; and wherein the coupler forms a dye with a peak absorption less than 565 nm.

2. An element as claimed in claim 1 characterized in that R, $R_1$ and $R_2$ are sufficiently lipophilic, singly or in combination, so as to render the coupler immobile in a photographic material.

3. An element as claimed in claim 1 R, $R_1$ and $R_2$ are the same or different and selected independently from unsubstituted or substituted alkyl, phenyl, naphthyl, pyridyl or quinolinyl.

4. An element as claimed in claim 3 wherein R is a phenyl.

5. An element as claimed in claim 3 wherein $R_1$ and $R_2$ are unsubstituted or substituted alkyl or substituted phenyl.

6. An element as claimed in claim 1 at least one of R, $R_1$ and $R_2$ is substituted, and the substituent(s) is selected independently from halogen, alkyl, aryl, heteroaryl, carboxylic acid, alkoxycarbonyl, aryloxycarbonyl, primary or secondary alkyl- or aryl-amido, alkyl- or aryl-sulfonamido, primary, secondary or tertiary amino, alkoxy, aryloxy, acyloxy, alkyl- or aryl-carbamoyl, alkyl- or aryl-sulfamoyl, alkyl- or aryl-sulfonyl or alkyl- or aryl-sulfonyloxy.

7. An element as claimed in claim 1 at least one of R, $R_1$ and $R_2$ includes a dye hue-shifting group which in the dye causes a hypsochromic dye shift.

8. An element as claimed in claim 7 wherein the dye hue-shifting group is selected such that the net shift is such that the coupler is suitable for use as a magenta coupler, forming a dye with a peak absorption less than 565 nm, in color photographic material.

9. An element as claimed in claim 8 wherein at least one of R, $R_1$ and $R_2$ is a substituted aryl group that includes at least one electron-donating substituent.

10. A photographic element as in claim 1 wherein the coupler has the following structure (II):

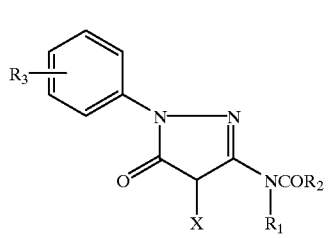

II wherein $R_3$ is H or one to five coupler-modifying functional groups which are the same or different.

11. An element as claimed in claim 10 wherein $R_3$ is at least one electron-donating group to provide a hypsochromic dye hue-shifting effect.

12. An element as claimed in claim 11 wherein said electron donating group(s) is positioned in the ortho- or para-position.

13. An element as claimed in claim 10 wherein $R_3$ represents one to three chloro-substituents.

14. An element as claimed in claim 1 wherein X is H.

15. An element as claimed in claim 1 wherein X is selected from halo, acyloxy, sulfonyloxy, aryloxy, heteroaryloxy, alkylthio, arylthio, heteroarylthio, aminocarbonyloxy or imido, or from a heterocyclic compound such as pyridone, pylidazinone, triazole, triazoledione, tetrazole, imidazole, pyrazole or benzotriazole.

16. An element as claimed in claim 15 wherein X is a substituted or unsubstituted phenylthio, particularly 2-[2-(2,4-dipentylphenoxy)butyramido]phenylthio.

17. A multi-color photographic material comprising a support bearing yellow, magenta and cyan image dye-forming units comprising at least one blue, green or red sensitive silver halide emulsion layer having associated therewith at least one yellow, magenta or cyan dye-forming coupler respectively, wherein at least one main image dye-forming coupler is an image dye-forming coupler as claimed in claim 1.

* * * * *